US006344339B1

(12) United States Patent
Menrad et al.

(10) Patent No.: US 6,344,339 B1
(45) Date of Patent: Feb. 5, 2002

(54) MONOCLONAL ANTIBODIES AGAINST THE EXTRACELLULAR DOMAIN OF HUMAN VEGF-RECEPTOR PROTEIN (KDR)

(75) Inventors: Andreas Menrad, Oranienburg; Karl-Heinz Thierauch, Berlin; Georg Martiny-Baron, Herbolzheim-Broggingen; Frank Totzke, Freiburg, all of (DE)

(73) Assignee: Schering Aktiengesellschaft, Berlin (DE)

(*) Notice: Subject to any disclaimer, the term of this patent is extended or adjusted under 35 U.S.C. 154(b) by 0 days.

(21) Appl. No.: 09/254,640

(22) PCT Filed: Sep. 9, 1997

(86) PCT No.: PCT/EP97/04928

§ 371 Date: May 19, 1999

§ 102(e) Date: May 19, 1999

(87) PCT Pub. No.: WO98/11223

PCT Pub. Date: Mar. 19, 1998

(30) Foreign Application Priority Data

Sep. 11, 1996 (DE) .......................................... 196 38 745

(51) Int. Cl.$^7$ ......................... G01N 33/53; C07K 16/28
(52) U.S. Cl. ...................... 435/7.94; 435/7.1; 435/7.92; 530/388.22; 530/387.9
(58) Field of Search .......................... 530/388.22, 387.9; 435/7.1, 7.92, 7.94

(56) References Cited

U.S. PATENT DOCUMENTS 5,861,499 A * 1/1999 Rockwell et al. ......... 536/23.53

FOREIGN PATENT DOCUMENTS

| WO | 94 11499 | 5/1994 |
| WO | 95 21868 | 8/1995 |

OTHER PUBLICATIONS

P. Rockwell Et Al.: "In vitro neutralization of vascular endothelial growth factor activation of flk–1 by a monoclonal antibody.", Molecular and Cellular Differentiation, vol. 3, No. 1, 1995, pp. 91–109.

P. Rockwell Et Al.: "Anti–tumor effects of a neutralizing monoclonal antibody to the tyrosine kinase receptor flk–1.", Proceedings of the American Association for Cancer Research, vol. 36, Mar. 1995, USA, p. 425.

B. Terman Et Al.: "Identification of the KDR tyrosine kinase as a receptor for vascular endothelial cell growth factor.", Biochemical and Biophysical Research Communications, vol. 187, No. 3, Sep. 30, 1992, Duluth, MN, pp. 1579–1586.

J. Waltenberger Et Al.: "Different signal transduction properties of KDR and flt1, two receptors for vascular endothelial growth factor.", The Journal of Biological Chemistry, vol. 269, No. 43, Oct 28, 1994, Baltimore, MD, pp. 236988–26995.

B. Millauer Et Al.: "High affinity VEGF binding and developmental expression suggest flk–1 as a major regulator of vasculogenesis and angiogenesis.", Cell, vol. 72, Mar. 26, 1993, Cambridge, MA, pp. 835–846.

A. Menrad Et Al.: "Novel antibodies directed against the extracellular domain of the human VEGF–receptor type ll.", Hybridoma, vol. 16, No. 5, 1997, New York, NY, pp. 465–471.

* cited by examiner

Primary Examiner—Lorraine Spector
(74) Attorney, Agent, or Firm—Millen, White, Zelano & Branigan, P.C.

(57) ABSTRACT

Monoclonal antibodies, secreted by hybridoma cell lines, that are directed against an epitope of the extracellular domain of human VEGF-receptor KDR, methods of determining human VEGF-receptor KDR in cell lysates or tissue analysates and the use of the antibodies in analytical assays, in diagnostics and as carrier molecules for therapeutic substances, are described.

18 Claims, 3 Drawing Sheets

1 2 3 4 5 6

MONOCLONAL ANTIBODIES AGAINST THE EXTRACELLULAR DOMAIN OF HUMAN VEGF-RECEPTOR PROTEIN (KDR)

The present invention relates to monoclonal antibodies, secreted by hybridoma cell lines, that are directed against an epitope of the extracellular domain of human VEGF-receptor KDR (kinase insert domain containing receptor), to methods of determining human VEGF-receptor KDR in cell lysates or tissue analysates and to the use of the antibodies in analytical assays, in diagnostics and as carrier molecules for therapeutic substances.

New vessels form as capillaries which sprout from existing small vessels. This process, known as angiogenesis, takes place in response to certain signals (Alberts et al., Molekularbiologie der Zelle, Verlag Chemie, Weinheim).

Angiogenesis is a process that is meticulously controlled by the interaction of vascular endothelial growth factor (vascular endothelial growth factor) and its corresponding highly affine KDR-receptor on endothelial cells. KDR has been characterised as a transmembranal tyrosine kinase receptor of sub-type 5 which serves as a key regulator of vascular endothelial cell development during embryogenesis and cell regeneration (Cancer and Metastasis Reviews 15: 159–163, 1996). Furthermore, the dysfunction of that normally meticulously regulated ligand-receptor interaction results in impairment of the angiogenesis process, which is a feature of many illnesses. Particularly important is that the growth of tumours and their metastases has proved to be angiogenesis-dependent to a high degree.

A monoclonal antibody having a limited reaction pattern is already known. That antibody is directed against the extracellular domain of mouse KDR-homologous flk-1 and is capable of neutralising the VEGF stimulation of a chimeric flk-1/fms-receptor that is expressed in transfected 3T3 cells (Rockwell et al., Molecular and Cellular Differentiation, 3 (1): 91–109 (1995)).

Monoclonal antibodies that can be used for a broad spectrum of analytical assays and methods of determining human VEGF-receptor KDR in cell lysates and tissue analysates using such antibodies have not been known hitherto.

The aim of the present invention is to provide monoclonal antibodies secreted by hybridoma cell lines. The monoclonal antibodies according to the invention can be used for a broad spectrum of analytical procedures and assays, in diagnostics and as carrier molecules for therapeutic substances.

There have now been prepared monoclonal antibodies that are directed against an epitope located within extracellular domains 1 to 7 of human VEGF-receptor KDR.

The present invention relates especially to monoclonal antibodies that are directed against an epitope located within extracellular domains 6 and 7 of human VEGF-receptor KDR.

The monoclonal antibodies AM 2-7-9, AM 2-10-1, AM 5-1-2 AM 5-10-13 and AM 2-4-1 are preferred.

The monoclonal antibodies AM 2-7-9 and AM 2-10-1 are especially preferred.

Those antibodies are directed specifically against an epitope that is located within extracellular domains 6 and 7 of human VEGF-receptor KDR.

The antibodies according to the invention exhibit a high degree of selectivity in a broad spectrum of analytical procedures and assays.

The monoclonal antibodies according to the invention have the advantage that they neither interfere with the ligand-binding domain nor activate KDR after binding.

The antibodies according to the invention are also valuable for diagnostic purposes.

For example, the monoclonal antibodies according to the invention can be used in Western blots, immunoprecipitation, ELISA, FACS analysis and in indirect immunofluoresence microscopy.

A further use of the monoclonal antibodies is in immunohistochemistry.

The monoclonal antibodies can also be used in screening for small agonistic and antagonistic molecules and in the detection of mutant receptor subtypes.

The monoclonal antibodies according to the invention can also be used in diagnostics, it being possible to couple them in combination with a suitable contrast-enhancing substance. The antibodies react with an epitope that is not located within the ligand-binding side of the KDR and is therefore capable of reacting with all KDR-receptor populations.

A preferred contrast-enhancing substance that can be coupled to the antibodies is technetium-99.

The monoclonal antibodies according to the invention can also be used in angiogenesis-dependent phenotypes, such as tumours and metastases thereof, rheumatoid arthritis or psoriasis, or pathological symptoms resulting therefrom, when coupled with suitable toxic substances.

Suitable toxic substances are adequately known to the person skilled in the art and are described, for example, in Byers & Baldwin, Immunology (1988), 65, 329–335 and in Blakey et al., Waldmann H. (ed): Moncclonal Antibody Therapy, Prog. Allergy. Basle, Karger, (1988), vol. 45, 50–90.

The invention relates also to the use of mRNA that codes for the heavy and the light chain of the antibodies according to the invention in the preparation of recombinant "single-chain antibodies".

The invention relates also to the use of the recombinant antibodies encoded by mRNA for Western blots, immunoprecipitation, ELISA and FACS analysis, in indirect immunofluoresence microscopy and immunohistochemistry and in screening for small agonistic and antagonistic molecules and in the detection of mutant receptor subtypes.

The invention relates also to a method of determining human VEGF-receptor KDR in cell lysates or tissue analysates, characterised in that 1. the monoclonal antibodies AM 2-7-9, 2-10-1, AM 5-1-2, AM 5-10-13 or AM 2-4-1, as captor antibodies, are coupled in purified form at a concentration of 1–10 μg/ml in coupling buffer on ELISA plates and then excess binding sites are blocked with blocking buffer,
2. cell or tissue analysates are prepared in a suitable lysis buffer,
3. the plates are washed in washing buffer before application of the lysates,
4. the KDR-protein to be determined in the sample is quantified using a recombinant KDR-protein as standard curve,
5. the tissue and cell lysates to be analysed are then introduced into the test system,
6. incubation is carried out at room temperature for 2 hours,
7. the ELISA plates are then washed.
8. determination of the "captured" KDR is carried out by means of a polyclonal anti-KDR antiserum and finally
9. detection by means of a chromogenic, chemiluminescent or radioactive substance is carried out.

The method can also take place in the form of a kinase test procedure that determines tyrosine-phosphorylated KDR.

In order to allow quantification of the test method, recombinant phosphorylated KDR can be used as the standard protein.

The determination of human VEGF-receptor KDR in cell lysates or tissue analysates can be carried out both qualitatively and quantitatively using the method.

The polyclonal anti-KDR antiserum used in step 8 of the method can be, for example, polyclonal anti-phosphotyrosine antiserum or a monoclonal anti-phosphotyrosine antibody.

The detection carried out in step 9 of the method can preferably be carried out with peroxidase-labelled secondary antibodies and suitable chromogenic or chemiluminescent substrates.

The antiserum used can be, for example, from goats or rabbits or from sheep, rats or donkeys, either directly in the form of enzyme-labelled immunoglobulin or indirectly by means of enzyme-labelled anti-goat, anti-rabbit, anti-sheep, anti-rat or anti-donkey antibodies. Either alkaline phosphatase or peroxidase is used for that purpose.

The ELISA plates used in step 1 of the method can be antibody-coated and blocked.

The lysis buffer used in step 2 of the method contains 1–5 mM divalent ions and 1–15% glycerol.

The lysis buffer preferably contains 1–2 mM divalent ions and 5–12% glycerol.

A lysis buffer that contains 1.5 mM divalent ions and 10% glycerol is especially preferred.

A preferred divalent ion is, for example, magnesium.

The washing and dilution buffers used in the method can be any buffers known to the person skilled in the art for that purpose.

Preferred washing buffers are those containing PBS with 0.05% detergent and 0.1% bovine serum albumin.

Preferred dilution buffers are those containing 1% bovine serum albumin.

The following Examples describe the preparation of monoclonal antibodies according to the invention and use thereof, but the invention is not limited to these Examples.

1. Preparation of Monoclonal Antibodies

Female Balb/c mice (six weeks old) are hyper-immunised either with soluble receptor (20 µg/injection) in Freund's complete adjuvant or with bacculovirus-infected SF-9 cells ($10^7$ cells/injection in PBS) that express the full-length human KDR receptor protein. Specific antibody titres are determined using the extracellular KDR domain by ELISA. Three days after the last immunisation the spleen is removed. The splenocytes are fused with SP20.Ag.14 murine myeloma cells in accordance with known methods (Köhler and Millstein, Nature 256, 495, 1975). The colonies formed are screened by means of ELISA and Western blot using the soluble extracellular KDR domain. Positive colonies are cloned three times by limited dilution, purified with protein A/Sepharose chromatography and further characterised.

2. Use in Western Blots

Figure 1:
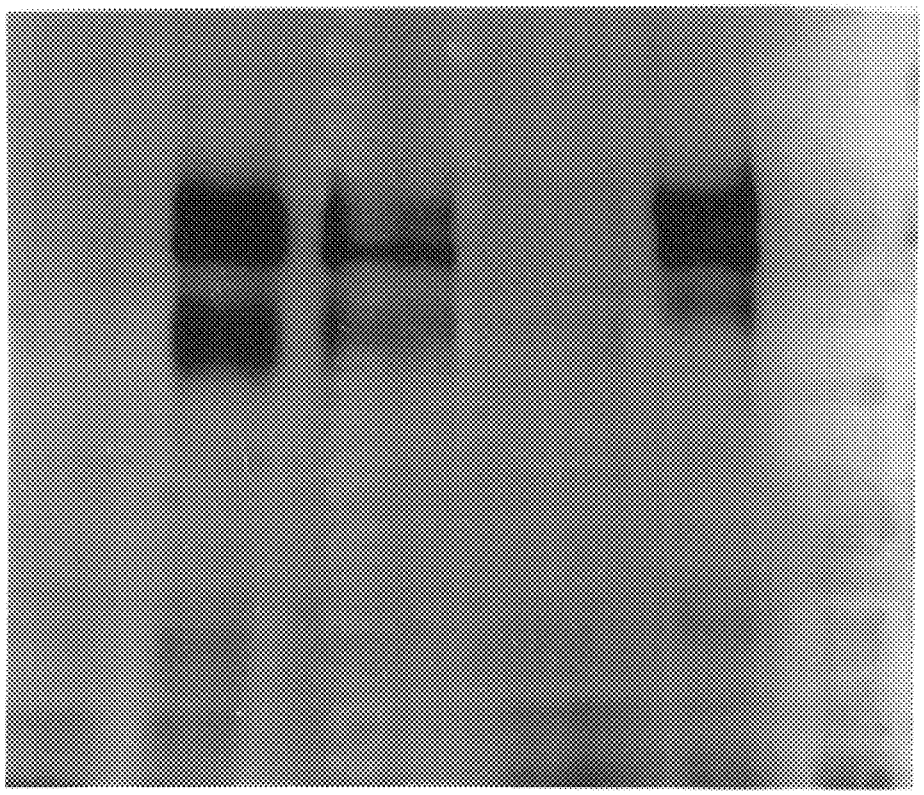
FIG. 1 shows a gel with the specific reaction pattern using the example of the monoclonal antibody AM 2-10-1:
track 1: pig aorta endothelial cells, 25 µg total cell lysate
track 2: pig aorta endothelial cells, transfected with human KDR, 25 µg total cell lysate
track 3: CHO cells, transfected with human KDR, 25 µg total cell lysate
track 4: CHO cells, 25 µg total cell lysate
track 5: human umbilical cord endothelial cells, passage 6, 25 µg total cell lysate
track 6: mouse endothelial cells, 25 µg total cell lysate

Complete cell lysates are prepared by lysis in a suitable lysis buffer that contains the above-described concentration of divalent ions and glycerol. Equal amounts of protein are separated by means of polyacrylamide gel electrophoresis under nonreducing conditions, transferred to nitrocellulose and probed with the monoclonal antibodies AM 2-7-9 and AM 2-10-1 in accordance with procedures known per se. The visualisation of the immunoreactive bands is carried out either by means of chemiluminescence or enzymatically, using alkaline-phosphatase-labelled secondary antibodies and corresponding chromogenic substrates. FIG. 1 shows the gel of a Western blot.

3. Use in Immunoprecipitation

Figure 2:
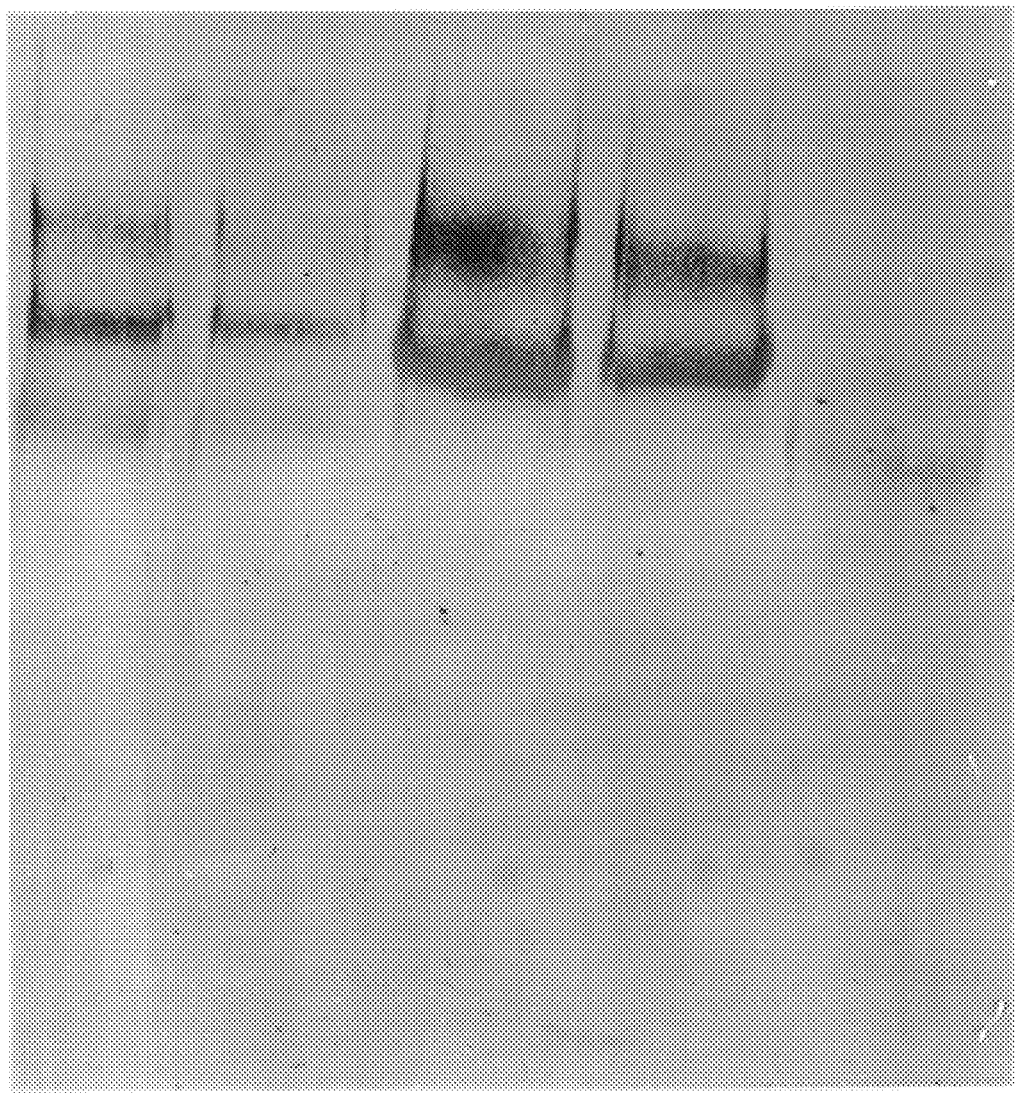
FIG. 2 shows the gel for immunoprecipitation with the monoclonal antibodies AM 2-10-1 and AM 2-7-9:
track 1: 5 µg AM 2-7-9
track 2: 1 µg AM 2-7-9
track 3: 5 µg AM 2-10-1
track 4: 1 µg AM 2-10-1
track 5: isotype control, 10 µg non-specific antibody of subclass IgG1

Immunoprecipitations are carried out using a suitable lysis buffer (50 mM Tris-HCl pH 7.4, 150 mM NaCl, 1% IGEPAL® CA-630, 10% (v/v) glycerol, 1.5 mM $MgCl_2$, 1 mM EGTA, 5 mM EDTA, 50 mM NaF, 2 mM sodium ortho-vanadate) and complete protease inhibitors in accordance with known methods. FIG. 2 shows the gel of the immunoprecipitation.

4. Use in Immunohistochemistry

Cells are cultured on sterile cover glasses until shortly before confluence and are fixed with formaldehyde (4% v/v PBS per 4 g per litre glucose) before or after incubation with 20 µg/ml of the corresponding antibody in PBS. The immunoreaction is visualised with alkaline-phosphatase-labelled secondary antibodies and fast naphthol red as chromogenic substrate.

5. Epitope Mapping

Figure 3:
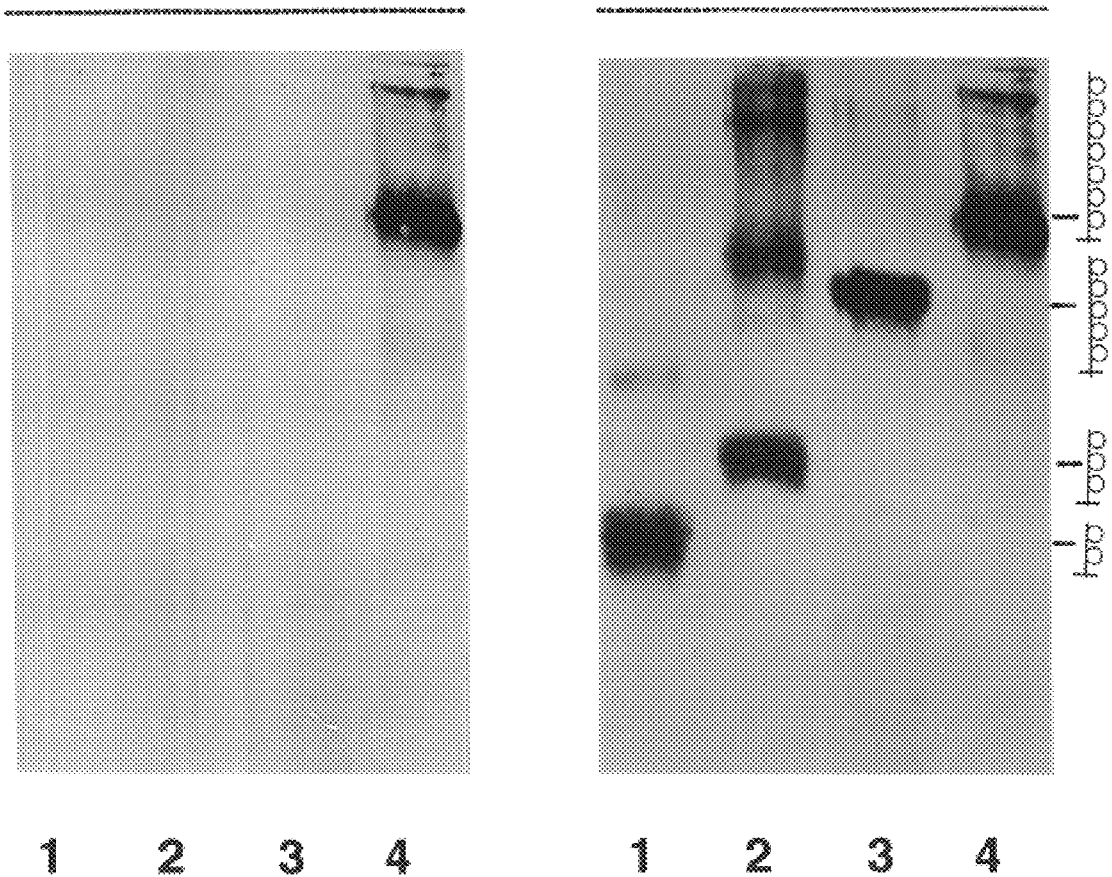
FIG. 3 shows epitope mapping:
track 1: soluble KDR, domains 1 and 2
track 2: soluble KDR, domains 1 to 3
track 3: soluble KDR, domains 1 to 5
track 4: soluble KDR, domains 1 to 7

2 µg portions of recombinant soluble KDR-receptor domains that are provided with a "myc-tag" are separated by SDS-PAGE (10%) and transferred to nitrocellulose. Then two identical films are incubated with the monoclonal antibody AM 2-10-1 or with a monoclonal anti-myc antibody. Immunocomplexes are visualised by alkaline-phosphatase-labelled secondary antibodies (see FIG. 3).

What is claimed is:

1. A monoclonal antibody that is directed against an epitope located within extracellular domains 1–7 of human VEGF-receptor KDR and is not reactive with the ligand binding site of the VEGF-receptor KDR.

2. A monoclonal antibody according to claim 1, wherein said antibody is directed against an epitope located within extracellular domain 6 or extracellular domain 7 of human VEGF-receptor KDR.

3. A method for identifying epitopes located within the extracellular domains 1–7 of the VEGF-receptor KDR comprising reacting the monoclonal antibody according to claim 1 with a sample containing a VEGF-receptor KDR in a Western Blot assay, a immunoprecipitation assay, an ELISA assay, a FACS assay or an indirect immunofluorescence assay.

4. A method for identifying epitopes located within the extracellular domains 1–7 of the VEGF-receptor KDR comprising reacting the monoclonal antibody according to claim 1 with cells expressing the VEGF-receptor KDR in an immunohistochemistry assay.

5. A method for screening small agonistic and antagonistic molecules in the detection of mutant receptor subtypes comprising assaying cells for the mutant receptor by reacting said cells with the monoclonal antibody according to claim 1.

6. A method for diagnosing cells bearing VEGF-receptor KDR comprising reacting said cells with the monoclonal antibody according to claim 1 wherein the method is an immunological method.

7. The method according to claim 6, wherein the monoclonal antibody is coupled to a suitable substrate contrast-enhancing substance.

8. The method according to claim 7, wherein the contrast-enhancing substance coupled to the antibody is technetium-99.

9. A method of determining human VEGF-receptor KDR in a cell lysate or tissue analysate comprising:

(a) coupling a monoclonal antibody which is directed against an epitope located within the extracellular domains 1–7 of human VEGF-receptor KDR, but is not reactive with the ligand binding site of the VEGF-receptor KDR, in purified form at a concentration of 1–10 $\mu$g/ml in coupling buffer, to an ELISA plate and then blocking excess binding sites with a blocking buffer, (b) preparing a cell or tissue analysate in a suitable lysis buffer, (c) washing the ELISA plate in washing buffer before application of the analysate, (d) introducing the cell or tissue analysate of step (b) to be analysed into said ELISA plate to form a test system, (e) incubating the test system to allow VEGF-receptor KDR to bind said monoclonal antibody and thus to capture said VEGF-receptor KDR, (f) washing the ELISA plate to remove unbound material, and (g) detecting the captured VEGF-receptor KDR using a secondary antibody in a chromogenic, chemiluminescent or radioactive assay system.

10. The method according to claim 9, wherein the VEGF-receptor KDR can be assayed using a kinase assay.

11. The method according to claim 9, wherein recombinant phosphorylated KDR is used as the standard protein.

12. The method according to claim 9, wherein the second antibody is an anti-phosphotyrosine antibody.

13. The method according to claim 12, wherein the anti-phosphotyrosine antibody is monoclonal.

14. The method according to claim 9, wherein the substance used for detection in step i of the method is a peroxidase-labeled secondary antibody which is then detected by using a suitable chromogenic or chemiluminescent substrates.

15. The method according to claim 9, wherein the lysis buffer used in step b of the method contains from 1 to 5 mM divalent ions and from 1 to 15% glycerol.

16. The method according to claim 15, wherein the divalent ion is magnesium.

17. The method according to claim 9, wherein the lysis buffer used in step b of the method contains from 1 to 2 mM divalent ions and from 5 to 12% glycerol.

18. The method according to claim 9, wherein the lysis buffer used in step b of the method contains 1.5 mM divalent ions and 10% glycerol.

* * * * *